US011883675B2

(12) United States Patent
Hess et al.

(10) Patent No.: US 11,883,675 B2
(45) Date of Patent: Jan. 30, 2024

(54) TRANSCUTANEOUS ENERGY TRANSFER SYSTEM INCLUDING ALARM

(71) Applicant: Medtronic, Inc., Minneapolis, MN (US)

(72) Inventors: Michael F. Hess, Minneapolis, MN (US); Michael A. Reinert, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 491 days.

(21) Appl. No.: 17/107,419

(22) Filed: Nov. 30, 2020

(65) Prior Publication Data

US 2021/0187309 A1 Jun. 24, 2021

Related U.S. Application Data

(60) Provisional application No. 62/951,230, filed on Dec. 20, 2019.

(51) Int. Cl.
*A61N 1/378* (2006.01)
*A61N 1/372* (2006.01)

(52) U.S. Cl.
CPC ....... *A61N 1/3787* (2013.01); *A61N 1/37282* (2013.01); *A61M 2205/18* (2013.01); *A61M 2205/8206* (2013.01); *A61M 2205/8243* (2013.01)

(58) Field of Classification Search
CPC .............. A61N 1/3787; A61N 1/3782; A61M 2205/18; A61M 2205/8206; A61M 2205/8243
See application file for complete search history.

(56) References Cited

U.S. PATENT DOCUMENTS

| 10,143,788 | B2 | 12/2018 | Rudser et al. |
| 2007/0270921 | A1 | 11/2007 | Strother et al. |
| 2012/0157755 | A1 | 6/2012 | D'Ambrosio |
| 2015/0290373 | A1 | 10/2015 | Rudser et al. |
| 2015/0294550 | A1 | 10/2015 | Kimball et al. |
| 2017/0246366 | A1 | 8/2017 | Rudser |

(Continued)

OTHER PUBLICATIONS

PCT/US2020/063565, The International Search Report and Written Opinion, dated Feb. 26, 2021, 10pages.

(Continued)

*Primary Examiner* — Joseph M Dietrich
(74) *Attorney, Agent, or Firm* — Shumaker & Sieffert, P.A.

(57) ABSTRACT

Various embodiments of a transcutaneous energy transfer system are disclosed. The system includes an internal component adapted to be disposed within a body of a patient and an external component adapted to be disposed outside the body of the patient. The external component includes an external controller that is adapted to determine whether an internal coil of the internal component is electromagnetically disconnected from an external coil of the external component. If electromagnetically disconnected, then the external controller is adapted to determine a reconnection time threshold based upon at least one of a power transfer efficiency value between the internal coil and the external coil, a charge state of an internal power source, or a power consumption value of an implantable device, and output a charging alarm if a time interval when the internal coil is electromagnetically disconnected from the external coil exceeds the reconnection time threshold.

20 Claims, 3 Drawing Sheets

(56) References Cited

U.S. PATENT DOCUMENTS

2018/0114426 A1    4/2018  Lee
2019/0231953 A1    8/2019  Kadrolkar et al.
2021/0220639 A1    7/2021  Schiling et al.

OTHER PUBLICATIONS

International Preliminary Report on Patentability from International Application No. PCT/US2020/063565, dated Jun. 30, 2022, 8 pp.

TRANSCUTANEOUS ENERGY TRANSFER SYSTEM INCLUDING ALARM

CROSS-REFERENCE TO RELATED APPLICATIONS

This application claims the benefit of U.S. Provisional Application No. 62/951,230, filed Dec. 20, 2019, the disclosure of which is incorporated by reference herein in its entirety.

TECHNICAL FIELD

This disclosure generally relates to a transcutaneous energy transfer system that includes an alarm and an implantable device that is implantable within a patient.

BACKGROUND

Transcutaneous energy transfer (TET) systems are used to supply power to devices such as pumps implanted within a human body. A magnetic field generated by a transmitting coil outside the body can transmit power across a cutaneous (skin) barrier to a magnetic receiving coil implanted within the body. The receiving coil can then transfer the received power to the implanted pump or other implantable devices and to one or more power sources (e.g., batteries) implanted within the body to charge the power source. Such systems efficiently generate and wirelessly transmit a sufficient amount of energy to power one or more implanted devices while maintaining the system's efficiency and overall convenience of user.

TET systems can be utilized, e.g., with ventricular assist devices (VADs) that include implantable blood pumps that are used when a patient's heart is unable to provide adequate circulation to the patient's body, thereby leading to heart failure. Such patients may use a VAD while awaiting a heart transplant or for longer periods of time. Further, some patients may use a VAD while recovering from heart surgery. Such VADs typically include implanted power sources that can be charged, e.g., by a TET system.

SUMMARY

The techniques of this disclosure generally relate to various embodiments of a transcutaneous energy transfer system and a method of using such system. The system can include one or more controllers that are adapted to provide a charging alarm to at least one of a patient, caregiver, or clinician that indicates that charging of an internal power source of the system that is implanted within the patient's body should commence. Such charging of the internal power source should resume before the power source is depleted and an implantable device such as a blood pump that is electrically connected to the internal power source ceases to operate.

In one example, aspects of this disclosure relate to a transcutaneous energy transfer system that includes an internal component adapted to be disposed within a body of a patient. The internal component includes an internal coil, an internal power source electrically connected to the internal coil and adapted to receive power from the internal coil, an implantable device electrically connected to the internal power source, and internal circuitry including an internal transceiver adapted to send and receive signals representative of one or more parameters relating to operation of the internal component. The system also includes an external component adapted to be disposed outside the body of the patient. The external component includes an external coil, an external power source electrically connected to the external coil, and external circuitry electrically connected to the external power source and the external coil. The external circuitry includes an external transceiver and an external controller, where the external transceiver is adapted to communicate with the internal transceiver and send and receive the signals representative of the one or more parameters relating to operation of the internal component. Further, the external controller is electrically connected to the external transceiver and adapted to determine whether the internal coil is electromagnetically disconnected from the external coil. If the internal coil is electromagnetically disconnected from the external coil, then the external controller is adapted to determine a reconnection time threshold based upon at least one of a power transfer efficiency value between the internal coil and the external coil, a charge state of the internal power source, or a power consumption value of the implantable device; and output a charging alarm if a time interval when the internal coil is electromagnetically disconnected from the external coil exceeds the reconnection time threshold.

In another example, aspects of this disclosure related to a ventricular assist device that includes a transcutaneous energy transfer system. The transcutaneous energy transfer system includes an internal component adapted to be disposed within a body of a patient. The internal component includes an internal coil, an internal power source electrically connected to the internal coil and adapted to receive power from the internal coil, an implantable device electrically connected to the internal power source, and internal circuitry including an internal transceiver adapted to send and receive signals representative of one or more parameters relating to operation of the internal component. The system also includes an external component adapted to be disposed outside the body of the patient. The external component includes an external coil, an external power source electrically connected to the external coil, and external circuitry electrically connected to the external power source and the external coil. The external circuitry includes an external transceiver and an external controller, where the external transceiver is adapted to communicate with the internal transceiver and send and receive the signals representative of the one or more parameters relating to operation of the internal component. Further, the external controller is electrically connected to the external transceiver and adapted to determine whether the internal coil is electromagnetically disconnected from the external coil. If the internal coil is electromagnetically disconnected from the external coil, then the external controller is adapted to determine a reconnection time threshold based upon at least one of a power transfer efficiency value between the internal coil and the external coil, a charge state of the internal power source, or a power consumption value of the implantable device; and output a charging alarm if a time interval when the internal coil is electromagnetically disconnected from the external coil exceeds the reconnection time threshold.

In another example, aspects of this disclosure relate to a method of outputting a charging alarm for a transcutaneous energy transfer system, including determining whether an internal coil of an internal component of the transcutaneous energy transfer system is electromagnetically disconnected from an external coil of an external component of the system. If the internal coil is electromagnetically disconnected from the external coil, then the method includes determining a reconnection time threshold based upon at least one of a power transfer efficiency value between the internal coil and the external coil, a charge state of an internal power source of the internal component that is electrically connected to the internal coil, or a power consumption value of an implantable device of the internal component that is electrically connected to the internal power source. The method further includes outputting the charging alarm if a time interval when the internal coil is disconnected from the external coil exceeds the reconnection time threshold.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The techniques of this disclosure generally relate to various embodiments of a transcutaneous energy transfer system and a method of using such system. The system can include one or more controllers that are adapted to provide a charging alarm to at least one of a patient, caregiver, or clinician that indicates that charging of an internal power source of the system that is implanted within the patient's body should commence. Such charging of the internal power source should resume before the power source is depleted and an implantable device such as a blood pump that is electrically connected to the internal power source ceases to operate.

Patients that have implantable devices such as ventricular assist devices (VADs) or left ventricular assist devices (LVADs) may receive notifications from such devices that power sources such as batteries contained within the devices are nearing depletion or are depleted. Upon receiving such notifications, the patient can recharge the power sources using any suitable technique or techniques, e.g., a transcutaneous energy transfer (TET) system. Notifications that are provided by a controller or other electronic component disposed within the implantable device may, however, be difficult for the patient to hear or detect. Further, external components that are associated with the implantable device may be disposed in a location where alarms provided by such external components can be difficult if not impossible for the patient to detect.

One or more embodiments of a TET system described herein can provide one or more alarms or notifications to at least one of a patient, caregiver, or clinician associated with the patient that indicate the critical need to initiate recharging of the implantable device before the implanted power source is depleted, thereby potentially leading to diminished capabilities of the implantable device.

Figure 1:
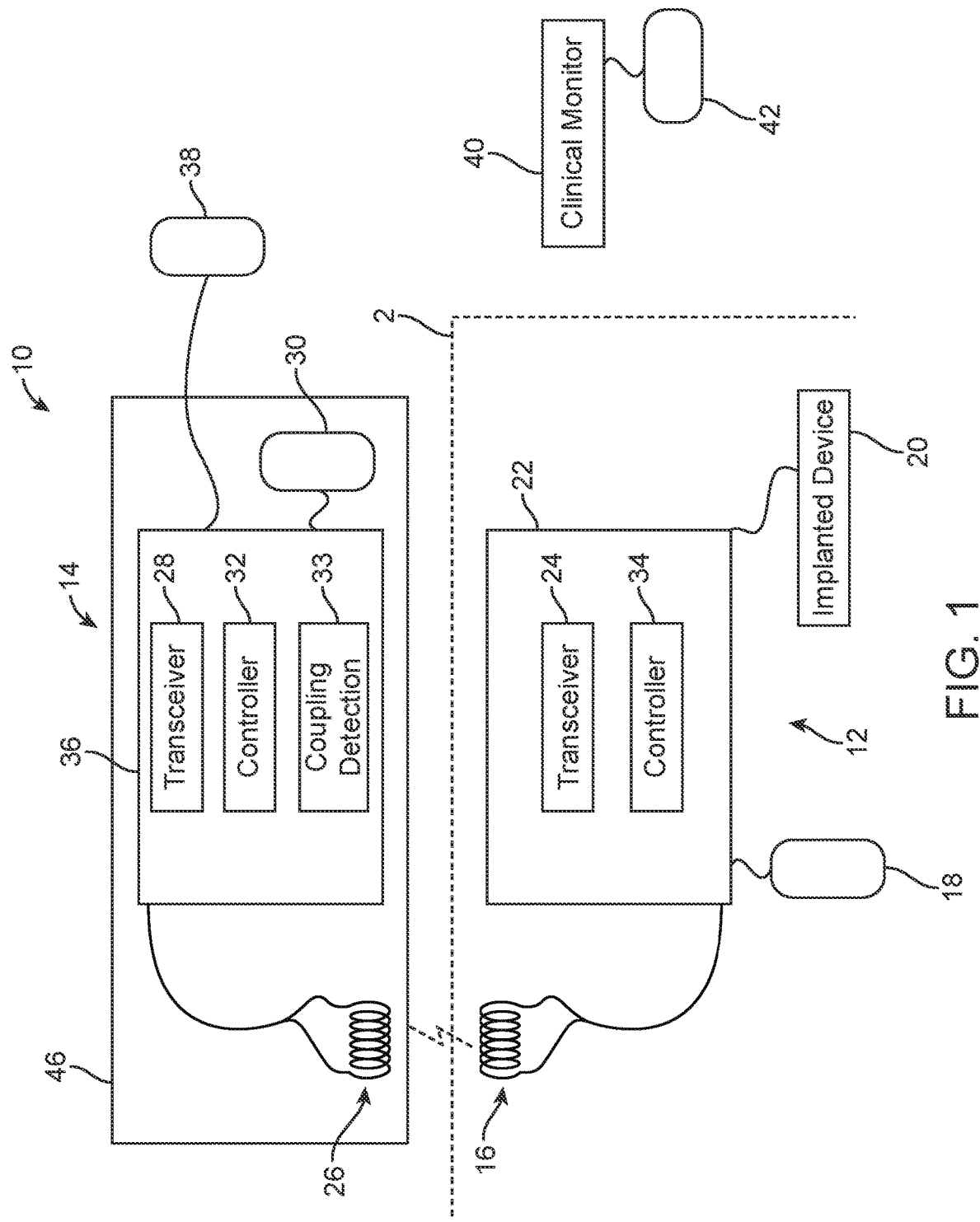
FIG. 1 is a schematic view of one embodiment of a transcutaneous energy transfer system.

FIG. 1 schematically illustrates a TET system 10. The system 10 includes an internal component 12 adapted to be disposed within a body 2 of a patient and an external component 14 adapted to be disposed outside the body of the patient. The internal component 12 includes an internal coil 16, an internal power source 18 electrically connected to the internal coil and adapted to receive power from the internal coil, and an implantable device 20 electrically connected to the internal power source. The internal component 12 also includes internal circuitry 22 that includes an internal transceiver 24 adapted to send and receive signals representative of one or more parameters relating to operation of the internal component.

Further, the external component 14 includes an external coil 26, an external power source 30 electrically connected to the external coil, and external circuitry 36 electrically connected to the external power source and external coil. The external circuitry 36 includes an external transceiver 28 and an external controller 32. The external transceiver 28 is adapted to communicate with the internal transceiver 24 and send and receive the signals representative of one or more parameters relating to operation of the internal component 12. Further, the external controller 32 is electrically connected to the external transceiver 28. As is further described herein, the external controller 32 is adapted to determine whether the internal coil 16 is electromagnetically disconnected from the external coil 26. If the internal coil 16 is electromagnetically disconnected from the external coil 26, then the external controller 32 is adapted to determine a reconnection time threshold based upon at least one of a power transfer efficiency value between the internal coil and the external coil, a charge state of the internal power source 18, or a power consumption value of the implantable device 20. Further, the external controller 32 is also adapted to output a charging alarm if a time interval when the internal coil 16 is electromagnetically disconnected from the external coil 26 exceeds the reconnection time threshold.

The internal component 12 of the system 10 can include any suitable elements or components that are disposed within the body 2 of the patient. One or more components of the internal component 12 can be disposed within a housing 52 (FIG. 3) as is described, e.g., in U.S. Patent Publication No. 2015/0290373 A1 to Rudser et al. and entitled TRANSCUTANEOUS ENERGY TRANSFER SYSTEMS. In one or more embodiments, one or more of the elements of the internal component 12 can be disposed independently from the housing 52 within the body 2 of the patient. For example, in one or more embodiments, one or more of the internal coil 16, the power source 18, the transceiver 24, and optional controller 34 can be disposed within the housing 52, and the implantable device 20 can be disposed outside of the housing independent from the other components but electrically connected to one or more of such components disposed within the housing.

As mentioned herein, the internal component 12 includes the internal coil 16 that is electrically connected to the power source 18 using any suitable technique or techniques. The internal coil 16 can include any suitable coil or device that can be electromagnetically connected (e.g., inductively connected) to the external coil 26 through an electromagnetic field to transfer energy or power wirelessly therebetween.

Electrically connected to the internal coil 16 is the internal power source 18. The internal power source 18 is adapted to receive power from the internal coil 16. The internal power source 18 can include any suitable power source or combination of power sources. In one or more embodiments, the internal power source 18 can include a lithium-ion cell/battery housed within a titanium or medical-grade plastic casing. In one or more embodiments, the internal power source 18 can include any suitable storage capacity. In one or more embodiments, the internal power source 18 is adapted to store any suitable charge needed for the system to operate as desired.

The internal power source 18 is electrically connected to the implantable device 20 to power the device. The internal power source 18 is also electrically connected to the internal circuitry 22 using any suitable technique or techniques. In one or more embodiments, energy received at the internal coil 16 is stored in the internal power source 18, provided to the implantable device 20, or both, via the internal circuitry 22. In one or more embodiments, energy stored at the internal power source 18 can be provided to the implantable device 20 via the internal circuitry 22.

Electrically connected to the internal power source 18 is the implantable device 20. The implantable device 20 can include any suitable implantable device, e.g., an implantable blood pump. In one or more embodiments, the implantable device 20 can include a pump such as for use in pumping blood as a ventricular assist device (VAD", for example. The implantable device 20 can include controlling circuitry to control, for example, a pump.

The implantable device 20 receives power from internal power source 18, the internal coil 16, or both. The implantable device 20 can have any suitable power requirements. Such power requirements can depend upon the nature of the device and may vary during operation of such device. For example, in one or more embodiments, systems for use with a typical VAD can be adapted to transmit at least 5 watts, at least 10 watts, at least 15 watts, or at least 20 watts of continuous power to the device 20.

The internal component 12 also includes internal circuitry 22. Such circuitry 22 can be electrically connected to at least one of the primary coil 16, the internal power source 18, or the implantable device 20 using any suitable technique or techniques. Further, such circuitry 22 can include any suitable device or components. For example, in one or more embodiments, internal circuitry 22 can include at least one of control circuitry (e.g., optional controller 34), RF telemetry (e.g., transceiver 24), voltage regulator circuitry, or power source selection circuitry as is described, e.g., in U.S. Patent Publication No. 2015/0290373 A1. In one or more embodiments, internal circuitry 22 can also include an optional controller 34 electrically connected to at least one of the transceiver 24, power source 18, or device 20. The controller 34 can include any suitable controller or controllers, e.g., controller 32 of external component 14 as is further described herein.

The transceiver 24 can include any suitable transceiver or transceivers that are adapted to send and receive signals representative of one or more parameters relating to operation of the internal component 12. The one or more parameters can include any suitable information regarding the internal component 12, e.g., charge state of the internal power source 18, operation state of the implanted device 20, operation state of the internal coil 16, thermal state of the internal component, etc.

The external component 14 of system 10 is adapted to be disposed outside the body 2 of the patient and can include any suitable devices or components for providing energy to the internal component 12. One or more of the devices or components of the external component 14 can be disposed within a housing 46. In one or more embodiments, one or more devices or components of the external component 14 can be disposed outside of or on the housing 46.

The external coil 26 of the external component 14 can include any suitable coil or coils, e.g., the same coil described herein regarding internal coil 16. In one or more embodiments, the external coil 26 can be disposed within a housing 44 as is further described herein. The external coil 26 can be of flexible or rigid construction and may have a size determined for optimal coupling to the internal coil. In one or more embodiments, the external coil 26 may be incorporated into a far-field wireless transmission network where the internal coil 16 is equipped to receive sufficient energy in this modality to affect the recharge of the implantable power source 18.

The external component 14 can further include one or more external power sources that are electrically connected to the external coil 26 and external circuitry 36. For example, the external component 14 can include external power source 30 that is electrically connected to the external coil 26 and external circuitry 36. In one or more embodiments, the external power source 30 can include a rechargeable battery. The external power source 30 can include any suitable power source or sources, e.g., the same power sources described herein regarding internal power source 18. In one or more embodiments, the external component 14 can also include a building power source 38 (such as AC power, or converted DC power, supplied from an electrical outlet in a building). In one or more embodiments, the external power source such as building power source 38 can include an AC to DC power converter. The external power sources 30, 38 can supply any suitable input voltage, e.g., at least about 20V and no greater than about 250V.

The external circuitry 36 of the external component 14 is electrically connected to the external power source 30, 38 and the external coil 26. Such circuitry 36 can include any suitable elements or components, e.g., the same elements or components described herein regarding internal circuity 22 of internal component 12. The external circuitry 36 includes the transceiver 28 and the external controller 32.

The external transceiver 28 of the external component 14 is adapted to communicate with the internal transceiver 24 and send and receive the signals representative of the one or more parameters relating to operation of the internal component. In one or more embodiments, the external transceiver 28 can be adapted to send and receive signals representative of one or more parameters relating to operation of the external component. The external transceiver 28 can include any suitable transceiver or transceivers, e.g., the same transceivers described herein regarding internal transceiver 24.

Electrically connected to the external transceiver 28 is the external controller 32. The external controller 32 can include any suitable controller or controllers. In one or more embodiments, the external controller 32 can include one or more processors, memory, input devices, output devices, sensors, power sources, etc.

Further, the external controller 32 can includes data storage that allows for access to processing programs or routines and one or more other types of data that may be employed to carry out the exemplary techniques, processes, and algorithms of the present disclosure. For example, processing programs or routines may include programs or routines for performing computational mathematics, matrix mathematics, Fourier transforms, compression algorithms, calibration algorithms, image construction algorithms, inversion algorithms, signal processing algorithms, normalizing algorithms, deconvolution algorithms, averaging algorithms, standardization algorithms, comparison algorithms, vector mathematics, analyzing optical sensor data, analyzing laser singulation settings, controlling an emitting device, detecting substrate surface defects, or any other processing required to implement one or more embodiments as described herein.

In one or more embodiments, the external controller 32 can utilize one or more computer programs executed on programmable computers, such as computers that include, for example, processing capabilities (e.g., microcontrollers, programmable logic devices, etc.), data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The programs used to implement the processes described herein may be provided using any programmable language, e.g., a high-level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein.

In view of the above, it will be readily apparent that the functionality as described in one or more embodiments according to the present disclosure may be implemented in any manner as would be known to one skilled in the art. As such, the computer language, the computer system, or any other software/hardware that is to be used to implement the processes described herein shall not be limiting on the scope of the systems, processes or programs (e.g., the functionality provided by such systems, processes or programs) described herein.

The techniques described in this disclosure, including those attributed to the systems, or various constituent components, may be implemented, at least in part, in hardware, software, firmware, or any combination thereof. For example, various aspects of the techniques may be implemented by the external controller 32, which may use one or more processors such as, e.g., one or more microprocessors, DSPs, ASICs, FPGAs, CPLDs, microcontrollers, or any other equivalent integrated or discrete logic circuitry, as well as any combinations of such components, image processing devices, or other devices. The term "processing apparatus," "processor," or "processing circuitry" may generally refer to any of the foregoing logic circuitry, alone or in combination with other logic circuitry, or any other equivalent circuitry. Additionally, the use of the word "processor" may not be limited to the use of a single processor but is intended to connote that at least one processor may be used to perform the exemplary techniques and processes described herein.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by the external controller 32 to support one or more aspects of the functionality described in this disclosure.

The external circuitry 36 can further include any additional devices or components. For example, the external circuitry 36 can include at least one power source selection circuitry, drive circuitry, or a user interface. The power source selection circuitry is adapted to select an external power source (e.g., power source 30, building power source 38) from which to provide power to the external coil 26 and other components of the external circuitry 36. The drive circuit is adapted to drive the external coil 26 such that energy is transferred from the external coil to the internal coil 16 through an electromagnetic field. In one or more embodiments, the external circuitry 36 can also include a coupling detection circuit 33 that is adapted to provide an indication of whether the external coil 26 is electromagnetically coupled to the internal coil 16.

The system 10 may optionally include a clinical monitor 40 for collecting system parameters (e.g., implanted battery life, charge stored in implanted battery, alarms, pump data, patient health data, etc.) to be monitored, such as by the patient or by a hospital clinical staff. The clinical monitor 40 can include a memory, internal or external, for storing the collected parameters, as well as for logging an event history of the patient (e.g., a low flow condition, a no-flow or suction condition, an interrupt, etc.). The clinical monitor 40 can further be connected to and receive/transmit information to and from units other than the TET system, such as to and from the patient's watch or smartphone, or to and from a hospital computer database. The clinical monitor 40 can also be powered by its own dedicated power source or battery 42.

In some examples, the clinical monitor 40, aside from receiving and monitoring data from the other components of the TET system 10, can deliver set points or parameters (e.g., a flow rate) pertaining to the desired operation of the system 10. Such set points may be communicated to the external circuitry 36, internal circuitry 22, or both as an instruction for operating the system 10, and thereby utilized in setting further parameters of the system's operation, such as a pulse width and/or frequency for driving the wireless energy transmission to power the implanted device 20.

Figure 3:
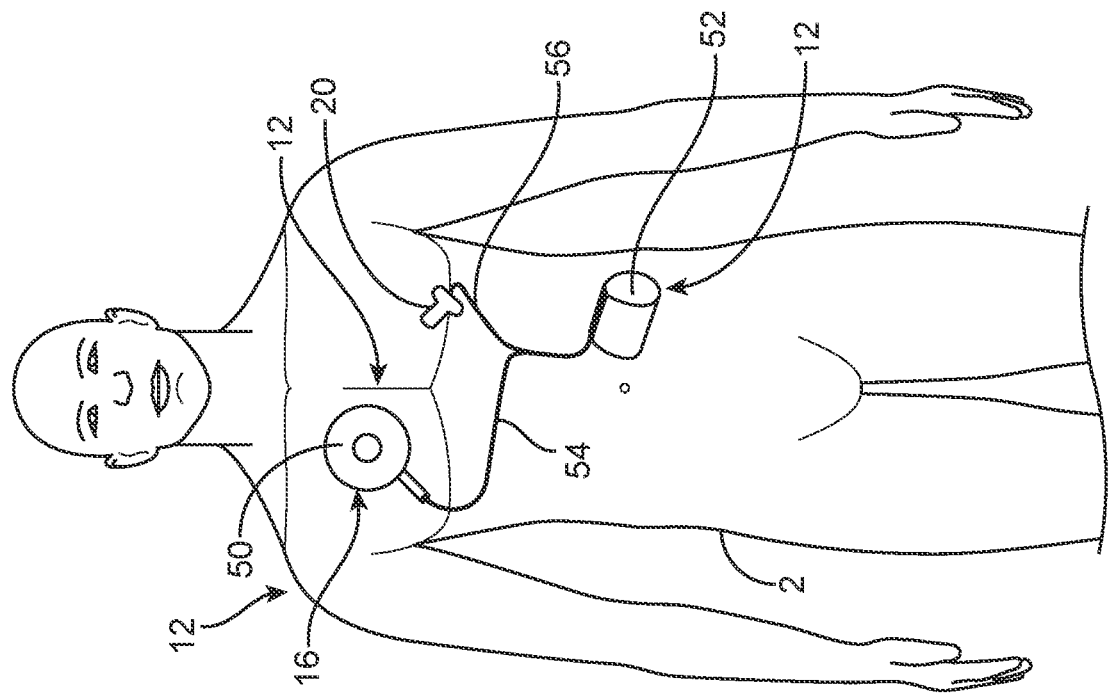
FIG. 3 is a schematic front view of an internal component of the transcutaneous energy transfer system of FIG. 1 disposed within a body of a patient.
Figure 2:
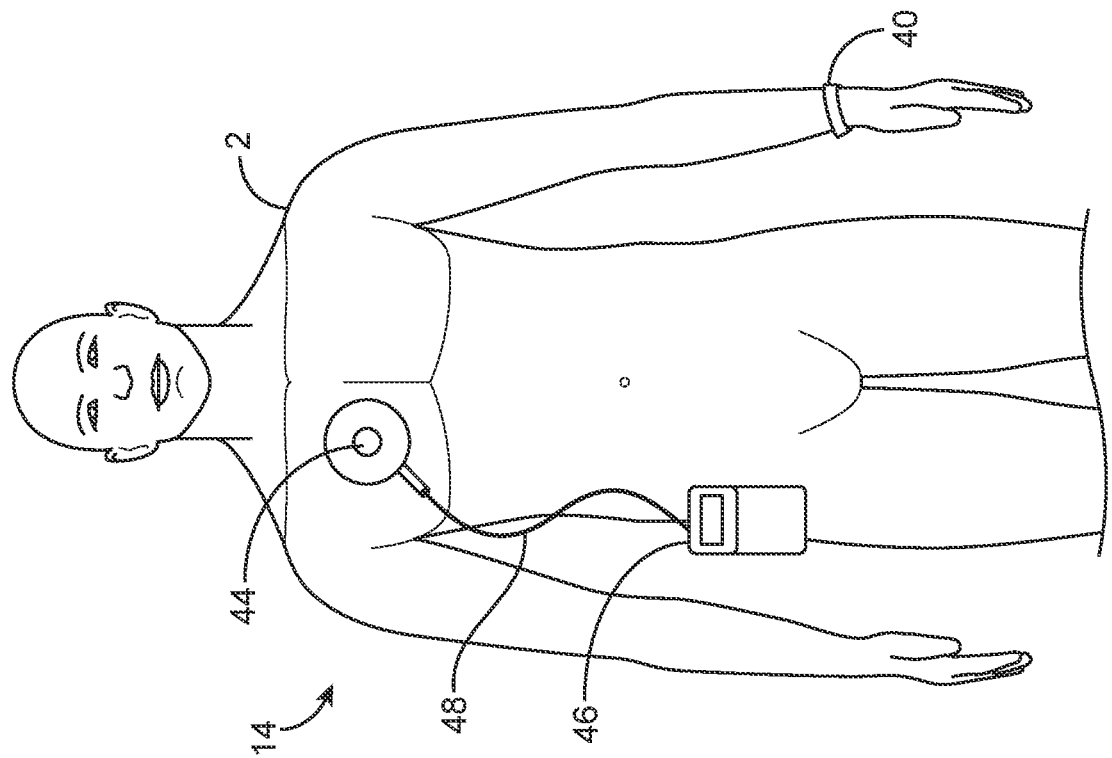
FIG. 2 is a schematic front view of an external component of the transcutaneous energy transfer system of FIG. 1.

FIG. 2 illustrates a schematic view of an exemplary arrangement of the external component 14 of the system 10, and FIG. 3 illustrates a schematic view of an exemplary arrangement of the internal component 12 of the system implanted within the patient.

The external component 14 can include the housing 46 and the external coil 26. In one or more embodiments, the external coil 26 can be disposed in a separate housing 44 from the housing 46. The housing 46 can be disposed in any suitable location relative to the patient's body 2, e.g., around the patient's hip (e.g., in a pocket of the patient's clothing, mounted to a belt of the patient, etc.), and the external coil 26 can be located in any suitable location relative to the patient's body, e.g., on the patient's chest and secured in place by a garment worn by the patient, such as a sling or vest. The housing 46 of the external component and external coil 26 are further connected to each other by a wire 48. Also shown in FIG. 2 is the clinical monitor 40, which can be worn, e.g., on the patient's wrist. In other examples, the clinical monitor 40 can be located elsewhere, such as in the housing 46, or in the patient's smartphone, or not on the patient altogether.

In the embodiment illustrated in FIG. 2, the external power source 30 and external circuitry 36 can be disposed in the housing 46. In one or more embodiments, the external power source 30 can be disposed in a separate housing (e.g., separately mounted to the outside of the patient) and wired to the external circuitry 36 disposed within the housing 46.

As illustrated in FIG. 3, the internal component 12 can include the internal coil 16 disposed within a housing 50, the implantable device 20, and internal circuitry 22 disposed within housing 52 and electrically connected to the internal coil and the implantable device. In one or more embodiments, each of the circuitry 22, the implantable medical device 20, and the internal coil 16 can be disposed in a separate housing and dispersed throughout the patient's body 2 to accommodate the anatomy of the patient. For instance, in the embodiment illustrated in FIG. 3, the internal circuitry 22 is disposed within the housing 52 and mounted in the patient's chest. In one or more embodiments, the housing 50 of the internal coil 16 can be mounted to the patient's rib, back, or abdomen.

The internal coil 16 is electrically connected to the internal component 12 by a first cable 54, and the implantable device 20 is electrically connected to the internal circuitry by a second cable 56.

The internal coil 16 is disposed within the housing 50 and is adapted to be electromagnetically connected to the external coil 26. For example, the internal coil 16 can be adapted to be inductively coupled to the primary coil 26. Positioning of the internal coil 16 within the patient can be done in such a manner that makes mounting the external coil 26 in proximity to the secondary coil easy for the patient. For instance, the internal coil 16 can be positioned close to the skin of the patient. Moreover, the external coil 26 can be positioned close to a relatively flat part of the patient's body 2 to make mounting the external coil easier. In the embodiment illustrated in FIG. 3, the internal coil 16 is positioned close to the front of the patient's chest such that mounting the external coil 26 to the patient's chest places the external coil proximate the internal coil. In those examples where the housing 50 is mounted to the patient's rib, back, or abdomen, the external coil 26 can similarly be located close to the patient's skin, such that the internal coil 16 can be mounted in close proximity.

Figure 4:
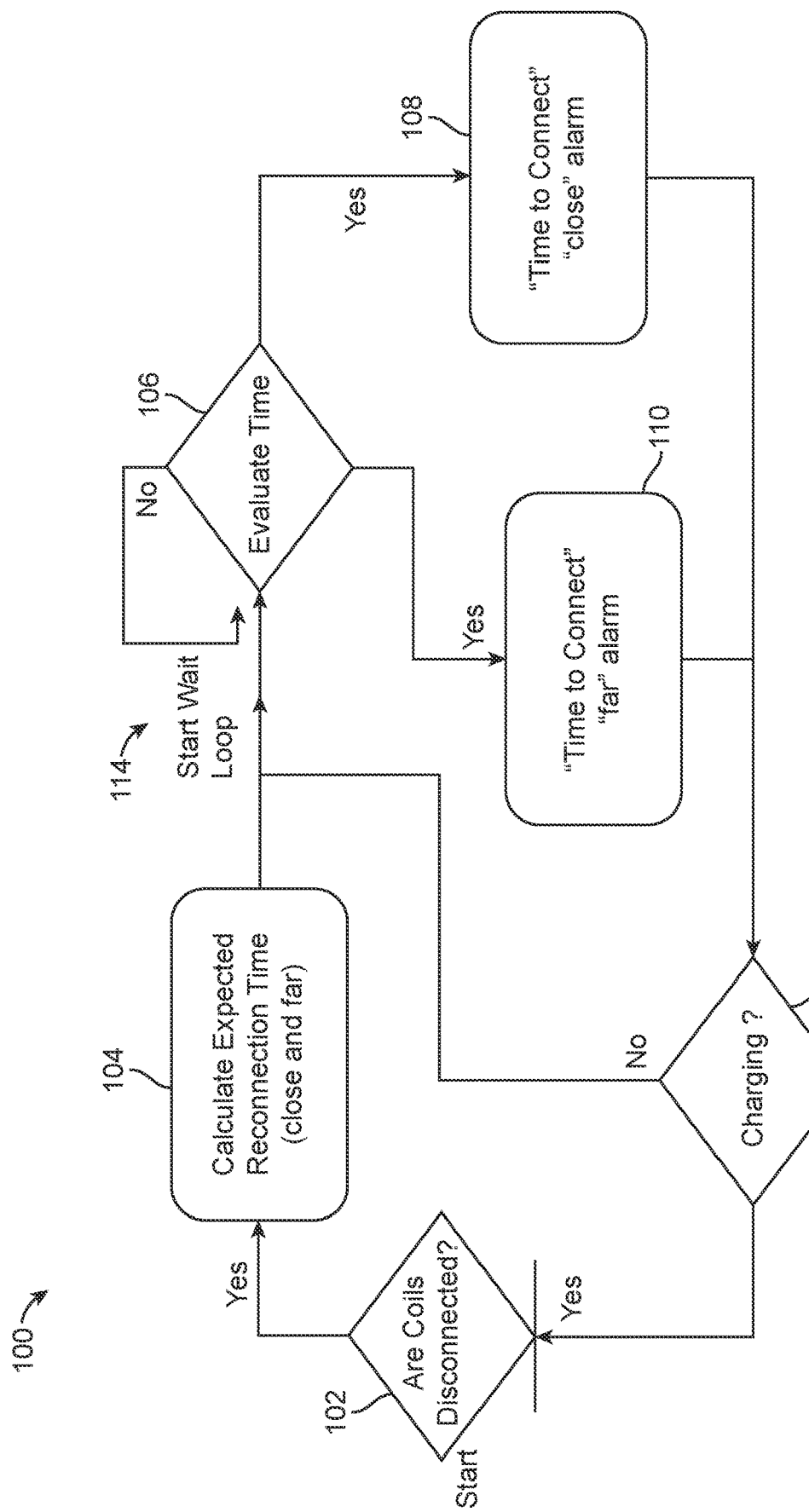
FIG. 4 is a flowchart of one embodiment of a method outputting a charging alarm for a transcutaneous energy transfer system.

Any suitable technique or techniques can be utilized to output a charging alarm for the transcutaneous energy system 10 of FIGS. 1-3. For example, FIG. 4 is a flowchart of one embodiment of a method 100 of providing an alarm or alarms to the patient. Although the method 100 is described regarding the transcutaneous energy transfer system 10 of FIGS. 1-3, such method can be utilized with any suitable transcutaneous energy transfer system.

The external controller 32 can be adapted to perform the method 100. In one or more embodiments, the internal controller 34 can be adapted to perform the method 100. Further, in one or more embodiments, both the external controller 32 and the internal controller 34 can be adapted to perform the method 100.

At 102, the external controller 32 is adapted to determine whether the internal coil 16 is electromagnetically disconnected from the external coil 26. Any suitable technique or techniques can be utilized to make this determination. For example, in one or more embodiments, the external circuitry 36 can include coupling detection circuitry 33 that is adapted to determine whether the internal and external coils 16, 26 are electromagnetically connected and the degree of such connection. In one or more embodiments, such coupling detection circuitry can receive information from a voltage detector indicating an amount of voltage in the external coil 26, and may determine connection between the coils 16, 26 based on the detected voltage. In one or more embodiments, the coupling detection circuitry 33 can receive telemetry signals from the internal circuitry 22 that indicates a current, Voltage, or other measure indicating coupling efficiency between the coils 16, 26. The coupling detection circuitry 33 can then determine an electromagnetic connection between the coils 16, 26 based on the telemetry signals (except in those examples where telemetry signals are not being received). The coupling detection circuitry 33 can also be adapted to aid the patient in properly aligning the coils 16, 26 as is further described in U.S. Patent Publication No. 2015/0290373 A1.

If the system 10 determines that the internal coil 16 is electromagnetically disconnected from the external coil 26, then the external controller 32 is further adapted to determine a reconnection time threshold at 104. As used herein, the term "reconnection time threshold" refers to a time value at which an alarm will be provided to the patient if the coils 16, 26 are not electromagnetically reconnected or coupled. The reconnection time threshold can be based upon the reconnection time, which is an interval calculated for both close and far states, where information such as the last known charging state of the internal power source 18, the age of the power source, the number of charging cycles encountered by the power source, and current implantable medical device power consumption rate are used to calculate a safe maximum duration before charging of the power source 18 should be reinitiated. As used herein, the term "close state" means a state where the external component 14 can determine that it is in proximity to the patient, e.g., by maintaining a regular communication link to the internal controller 34 via the internal transceiver 24 and the external transceiver 28. Further, the term "far state" refers to a state where the external component 14 can determine that it is not in proximity to the patient via the absence of a regular communication link between the internal component 12 and the external component.

Any suitable technique or techniques can be utilized to determine the reconnection time threshold. In one or more embodiments, the reconnection time threshold can be based upon at least one of a power transfer efficiency value between the internal coil 16 and the external coil 26, a charge state of the internal power source 18, or a power consumption value of the implantable device 20. Further, the reconnection time threshold can be based upon a time period for the patient to retrieve the external component 14 and electromagnetically connect the external coil 26 to the internal coil 16. Any suitable technique or techniques can be utilized to determine such time period. In one or more embodiments, the reconnection time threshold can also be based upon a charging history of the internal power source 18. Any suitable technique or techniques can be utilized to determine the charging history of the internal power source 18. In addition, the state of charge of the external component 14 may be considered. In the case of low charge level of the external power source 30, where a connection to line (AC) power may be required, the reconnection time threshold may have an additional safety factor applied to allow for time to locate and connect to an electrical outlet.

Any suitable technique or techniques can be utilized to determine the power transfer efficiency value between the internal coil 16 and the external coil 26, e.g., one or more of the techniques described in U.S. Patent Application Ser. No. 62/692,334, entitled INTEGRITY MONITORING FOR A TRANSCUTANEOUS ENERGY SYSTEM. In one or more embodiments, a wireless power transfer efficiency value measured over the predetermined period of time corresponds to a long term moving average. In one or more embodiments, the long term moving average indicates whether performance is degrading due to at least one non-alignment factor between the internal coil and external coil. In one or more embodiments, the at least one non-alignment factor includes at least one of increased fat thickness of a person in which the implantable power device is implanted and degradation of at least one material characteristics of the implantable power device. For example, increased fat thickness of a person may be caused by an increase in fatty tissue or subcutaneous fluid accumulation where the increased fat thickness may result in increased distance between the implanted coil and the skin surface. In one or more embodiments, the at least one non-alignment factor includes at least one characteristic of a person that causes the distance between the implanted coil and the skin surface (or external coil) to increase.

In one or more embodiments, the existence of the far state can be used to trigger an arbitrary time safety factor to be incorporated in setting the alarm. For example, if the system is determined to be in the far state the assumption could be set in the system to assume, e.g., at least 20 minutes will be required to reconnect the external charging system to couple to the internal coil 16. Additionally, location information derived from connectivity systems (e.g., Bluetooth®, WiFi, cellular based GPS) can be monitored and recorded to derive a projected physical distance, and from that, modulate the predicted time required to reacquire an external system for charging.

Further, any suitable technique or techniques can be utilized to determine a charge state of the internal power source 18. For example, a charge level of the internal power source 18 can be determined using any suitable technique or techniques by the internal controller 34. Such information can be transmitted to the external component 14 via the transceiver 24 of the internal component 12 and the transceiver 28 of the external component. Further, other information regarding the internal power source 18 can be determined by the internal controller 34. For example, the internal controller 34 can determine a charge capacity value of the internal power source 18. Further, the internal controller 34 can determine the number of charging cycles encountered by the internal power source 18 and compare that to a charge cycle threshold. In embodiments where the external power source 30 includes a rechargeable battery, the reconnection time threshold can also be based upon a charge state of the rechargeable battery. Any suitable technique or techniques can be utilized to determine this charge state.

Any suitable technique or techniques can be utilized to determine a power consumption value or values of the internal power source 18. As used herein, the term "power consumption value" the rate of discharge of the internal power source 18 as determined by the power level used to drive the implantable electronics and pump system. For example, a pump system configured to deliver 8 Watts of power to the LVAD system will consume internal stored energy faster than a system configured to deliver 5 Watts of power. This setting (or potential range of settings) is known to the external component 14 at the time of coil decoupling and will be used to compute the appropriate recharge time. One or more embodiments of techniques for determining power consumption trends of an implantable device such as a blood pump are described in U.S. patent application Ser. No. 16/248,888, entitled EARLY WARNING OF LVAD THROMBUS FORMATION, can be utilized to determine the power consumption value or values of the internal power source 18.

Any suitable technique or techniques can be utilized to combine, e.g., the values of power transfer efficiency between the internal coil and the external coil, a charge state of the internal power source, or a power consumption value of the implantable device and calculated a reconnection time threshold. For example, weighting can be applied to each of these values, and a reconnection time threshold can be calculated based upon these weighted values.

In one or more embodiments, the reconnection time threshold can include a far state reconnection time threshold and a close state reconnection time threshold. Any suitable technique or techniques can be utilized to determine the far state reconnection time threshold. In one or more embodiments, the far state reconnection time threshold can be determined based upon loss of communication between the external transceiver 28 and the internal transceiver 24. Further, the close state reconnection time threshold can be determined using any suitable technique or techniques. In one or more embodiments, the close state reconnection time threshold can be determined based upon maintained communication between the external transceiver 28 and the internal transceiver 24.

The external controller 32 can also be adapted to deactivate the charging alarm when the external coil 26 is electromagnetically reconnected with the internal coil 16. Further, in one or more embodiments, the external controller 32 can also be adapted to deactivate the charging alarm based upon a user input. Any suitable technique or techniques can be utilized to provide the user input. For example, in one or more embodiments, the external component 14 can include a display or keypad that can be utilized by the patient to provide the user input to the external controller 32 to deactivate the charging alarm. Further, in one or more embodiments, the external controller 32 can also be adapted to deactivate the charging alarm based upon a caregiver or clinician input. Any suitable technique or techniques can be utilized to provide the caregiver or clinician input to the external controller 32. For example, a clinician can provide input to the clinical monitor 40 that can then be transmitted to the transceiver 28 of the external component 14 using any suitable technique or techniques.

The charging alarm that is output by the external controller 32 can include any suitable alarm or alarms. In one or more embodiments, the charging alarm includes an audible alarm that can be heard by the patient to warn the patient that the external coil 26 should be electromagnetically connected to the internal coil 16 to provide power to the internal power source 18. In one or more embodiments, the charging alarm can include a voice recording that provides information to the patient, e.g., regarding the charge state of the internal power source 18. Further, in one or more embodiments, the charging alarm can include a vibratory alarm that provides a tactile notification to the patient that the internal power source 18 should be charged. In one or more embodiments, the external controller 32 can be adapted to transmit via the external transceiver 28 the charging alarm to at least one of a caregiver or a clinician. Further, in one or more embodiments, the external controller 32 can be adapted to transmit via the external transceiver 28 the charging alarm to a smart phone of the user of the system. The user can include the patient, a caregiver or a clinician. The external controller 32 can also adopt industry-standard broadcast techniques to communicate with all compatible devices within local range in an emergency mode operation.

At 104 of FIG. 4, an expected reconnection time for either the close state or the far state can be calculated using any suitable technique or techniques. A wait loop can then be initiated at 114 and the time interval can be evaluated at 106 using any suitable technique or techniques. If the time interval evaluated at 106 does not exceed the reconnection time threshold, then the wait loop is reinitiated at 114, and the time interval continues to be evaluated at 106. If, however, the reconnection time threshold is met at 106, then a charging alarm can be output at either 108 or 110 depending upon whether the close reconnection time threshold or the far reconnection time threshold has been met. For example, if the close reconnection time threshold has been met at 106, then the charging alarm for the close reconnection state can be provided by the external controller 32 at 108. Further, if the far reconnection time threshold has been met at 106, then the charging alarm for the far reconnection state can be provided at 110.

At 112, the external controller 32 can be adapted to determine whether the internal power source 18 is in a charge state. If the internal power source is in a charge state, then the method 100 returns to the coil connection state at 102. Although not shown, the external controller 32 can be adapted to deactivate the charging alarm at 112 if the internal power source 18 is in a charge state. If, however, the internal power source 18 is not being charged at 112, then the method 100 returns to the time evaluation state at 106.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A transcutaneous energy transfer system comprising:
    an internal component adapted to be disposed within a body of a patient, the internal component comprising:
        an internal coil;
        an internal power source electrically connected to the internal coil and adapted to receive power from the internal coil;
        an implantable device electrically connected to the internal power source; and
        internal circuitry comprising an internal transceiver adapted to send and receive signals representative of one or more parameters relating to operation of the internal component; and
    an external component adapted to be disposed outside the body of the patient, the external component comprising:
        an external coil;
        an external power source electrically connected to the external coil; and
        external circuitry electrically connected to the external power source and the external coil, wherein the external circuitry comprises an external transceiver and an external controller, wherein the external transceiver is adapted to communicate with the internal transceiver and send and receive the signals representative of the one or more parameters relating to operation of the internal component, and wherein the external controller is electrically connected to the external transceiver and adapted to:
            determine whether the internal coil is electromagnetically disconnected from the external coil;
            if the internal coil is electromagnetically disconnected from the external coil, then:
            determine a reconnection time threshold based upon at least one of a power transfer efficiency value between the internal coil and the external coil, a charge state of the internal power source, or a power consumption value of the implantable device; and
            output a charging alarm if a time interval when the internal coil is electromagnetically disconnected from the external coil exceeds the reconnection time threshold.

2. The transcutaneous energy transfer system of claim 1, wherein the external controller is further adapted to transmit via the external transceiver the charging alarm to at least one of a caregiver or a clinician.

3. The transcutaneous energy transfer system of claim 1, wherein the external controller is further adapted to transmit via the external transceiver the charging alarm to a smartphone of a user of the transcutaneous energy transfer system.

4. The transcutaneous energy transfer system of claim 1, wherein the reconnection time threshold comprises a far state reconnection time threshold and a close state reconnection time threshold, wherein the far state reconnection time threshold is further determined based upon loss of communication between the external transceiver and the internal transceiver, wherein the close state reconnection time threshold is further determined based upon maintained communication between the external transceiver and the internal transceiver.

5. The transcutaneous energy transfer system of claim 1, wherein the reconnection time threshold is further based upon a time interval for the patient to retrieve the external component and electromagnetically connected the external coil to the internal coil.

6. The transcutaneous energy transfer system of claim 1, wherein the external power source comprises a rechargeable battery, wherein the reconnection time threshold is further based upon a charge state of the rechargeable battery of the external power source.

7. The transcutaneous energy transfer system of claim 1, wherein the external controller further comprises a coupling detection circuit adapted to provide an indication of whether the external coil is electromagnetically connected to the internal coil.

8. The transcutaneous energy transfer system of claim 1, wherein the external controller is further adapted to deactivate the charging alarm when the external coil is electromagnetically reconnected with the internal coil.

9. A ventricular assist device comprising a transcutaneous energy transfer system that comprises:
  an internal component adapted to be disposed within a body of a patient, the internal component comprising:
    an internal coil;
    an internal power source electrically connected to the internal coil and adapted to receive power from the internal coil;
    an implantable device electrically connected to the internal power source; and
    internal circuitry comprising an internal transceiver adapted to send and receive signals representative of one or more parameters relating to operation of the internal component; and
  an external component adapted to be disposed outside the body of the patient, the external component comprising:
    an external coil;
    an external power source electrically connected to the external coil; and
    external circuitry electrically connected to the external power source and the external coil, wherein the external circuitry comprises an external transceiver and an external controller, wherein the external transceiver is adapted to communicate with the internal transceiver and send and receive the signals representative of the one or more parameters relating to operation of the internal component, and wherein the external controller is electrically connected to the external transceiver and adapted to:
      determine whether the internal coil is electromagnetically disconnected from the external coil;
      if the internal coil is electromagnetically disconnected from the external coil, then:
      determine a reconnection time threshold based upon at least one of a power transfer efficiency value between the internal coil and the external coil, a charge state of the internal power source, or a power consumption value of the implantable device; and
      output a charging alarm if a time interval when the internal coil is electromagnetically disconnected from the external coil exceeds the reconnection time threshold.

10. A method of outputting a charging alarm for a transcutaneous energy transfer system, the method comprising:
  determining that an internal coil of an internal component of the transcutaneous energy transfer system is electromagnetically disconnected from an external coil of an external component of the transcutaneous energy transfer system;
  determining a reconnection time threshold based upon at least one of a power transfer efficiency value between the internal coil and the external coil, a charge state of an internal power source of the internal component that is electrically connected to the internal coil, or a power consumption value of an implantable device of the internal component that is electrically connected to the internal power source; and
  outputting the charging alarm based on a time interval when the internal coil is disconnected from the external coil exceeding the reconnection time threshold.

11. The method of claim 10, wherein the charging alarm comprises an audible alarm.

12. The method of claim 10, wherein the charging alarm comprises a voice recording.

13. The method of claim 10, further comprising transmitting the charging alarm to at least one of a caregiver or a clinician.

14. The method of claim 10, further comprising transmitting the charging alarm to a smartphone of a user of the transcutaneous energy transfer system.

15. The method of claim 10, wherein the charge state of the internal power source comprises a charging history of the internal power source.

16. The method of claim 10, wherein the reconnection time threshold comprises a far state reconnection time threshold and a close state reconnection time threshold, wherein the far state reconnection time threshold is further determined based upon loss of communication between the external component and the internal component, wherein the close state reconnection time threshold is further determined based upon maintained communication between the external component and the internal component.

17. The method of claim 10, wherein the reconnection time threshold is further based upon a time period for a patient to retrieve the external component and electromagnetically connect the external coil to the internal coil.

18. The method of claim 10, wherein the reconnection time threshold is further based upon a charge state of a rechargeable battery of the external component that is electrically connected to the external coil.

19. The method of claim 10, further comprising deactivating the charging alarm when the external coil is electromagnetically reconnected with the internal coil.

20. They method of claim 10, further comprising deactivating the charging alarm based upon a caregiver or clinician input.

* * * * *